(12) United States Patent
Shin et al.

(10) Patent No.: US 7,193,076 B2
(45) Date of Patent: Mar. 20, 2007

(54) PLANT SENESCENCE-SPECIFIC GENE AND ITS PROMOTER

(75) Inventors: Jeong Sheop Shin, Seoul (KR); Kwang Wook Jung, Seoul (KR); Sung Han Ok, Seoul (KR); Sung Chul Bahn, Seoul (KR); Kyoung Shin Yoo, Seoul (KR); Min Kyung You, Seoul (KR)

(73) Assignee: Korea University Industry and Academy Cooperation Foundation

( * ) Notice: Subject to any disclaimer, the term of this patent is extended or adjusted under 35 U.S.C. 154(b) by 0 days.

(21) Appl. No.: 11/146,362

(22) Filed: Jun. 6, 2005

(65) Prior Publication Data

US 2006/0048241 A1    Mar. 2, 2006

(30) Foreign Application Priority Data

Sep. 2, 2004    (KR)    ............... 10-2004-0069765

(51) Int. Cl.
*A01H 1/00*     (2006.01)
*C07H 21/04*    (2006.01)
*C12N 5/14*     (2006.01)
*C12N 15/09*    (2006.01)

(52) U.S. Cl. .................. 536/24.1; 435/6; 435/468; 435/419; 435/253.3; 435/320.1; 435/536; 536/23.1; 800/278; 800/295

(58) Field of Classification Search ............... None
See application file for complete search history.

(56) References Cited

FOREIGN PATENT DOCUMENTS

| WO | WO 97/29123 | 8/1997 |
|----|-------------|--------|
| WO | WO 99/029159 | 6/1999 |
| WO | WO 02/016655 | 2/2002 |
| WO | WO 02/106655 A2 * | 2/2002 |
| WO | WO 02/48313 | 6/2002 |

OTHER PUBLICATIONS

Kim et al. (Plant Molecular Biology, 24:105-117, 1994).*
Oh et al., Plant J., Sep. 1997 12(3):527-35, "Identification of three genetic loci controlling leaf senescence in *Arabidopsis thaliana*".
Gepstein, et al., The Plant Journal (2003) 36, 629-642, "Large-scale identification of leaf senescence-associated genes".
NCBI GenBank Accession No. AF360331 "*Arabidopsis thaliana* unknown protein (At4g34120) mRNA, complete cds" Sep. 18, 2002. 2 pages.

* cited by examiner

*Primary Examiner*—Phuong T Bui
*Assistant Examiner*—Vinod Kumar
(74) *Attorney, Agent, or Firm*—Tuchman & Park LLC

(57) ABSTRACT

Disclosed herein is a novel gene which is isolated from *Arabidopsis thaliana* and shows senescence-specific expression. The expression of the gene is under the regulation of a promoter which is also disclosed herein. The gene in combination with the promoter can be utilized at the molecular level to control plant senescence in an environmentally friendly manner.

4 Claims, 5 Drawing Sheets

```
ctacctttgtttcttctctcagatttcataaagaaaagatttaatctttcattggaatctgtgagtaacagaggataagcgaat
ATGGGTTCAATCTCTTTATCCAATTCTATGCCCATAACTCGACTTCCACTACTT
ACATCACTCTATCATCAAAGCTTCCTTCCGATTTCTTCTTCATCTTTCTCTCTT
CTTCCTCTCTCTAATCGTCGTCGCTCCTCCACTTTTTCACCGTCAATCACCGTC
TCTGCCTTCTTCGCTGCTCCTGCCAGCGTTAATAATAATAACTCTGTTCCGGCA
AAAAATGGAGGTTACACAGTTGGGGATTTCATGACTCCGAGACAGAATTTGCA
CGTTGTTAAGCCCTCTACGTCGGTCGATGATGCGTTGGAACTTCTGGTTGAGAA
GAAAGTCACGGGATTGCCTGTAATTGACGATAATTGGACACTGGTTGGTGTTG
TTTCTGATTACGATTTGCTTGCATTGGACTCCATCTCTGGTCGCAGTCAAAATG
ATACAAACTTGTTCCCTGATGTCGACAGTACCTGGAAAACGTTTAACGAACTAC
AGAAACTGATCAGTAAGACATATGGAAAAGTTGTTGGAGACTTGATGACACCG
TCTCCTCTCGTTGTCCGTGATTCTACCAATTTAGAAGATGCAGCCAGGTTGCTT
CTGGAAACAAAGTTCCGAAGATTACCCGTTGTTGATGCTGATGGAAAACTGAT
TGGGATCCTTACAAGGGGAAACGTTGTAAGGGCTGCGCTGCAGATCAAACGGGA
AACCGAGAACTCTACATAGctaggaagcagcagtgatggagcagatctgaatctgccatagttaatagcg
aaatctatttattccattgatataagtatatatgtaaccattctctgtcaatttcggttttcagaagcaattttgttactttagg
agtaacatttctcagactcggaactgaagacaaatggtatatttgatacatatatgtttattgtagcacaggtctactcttatc
accaagacaaagactaagcagaatcgaactaattttcaatttcttactgaggtcttttcaatgaagctattcaaatcgagaa
acgaagacccttttttctccaccgccggctttggccatcacagcctcttctctgccatattctctgctta
```

FIG.2

```
GTGTTCACGGAAGATGAATTTGATTACCAATAAGGCCAATGCTGGTGATCCCCC
TCTTTGGCCTTTTGACTGTTGGTGGTTGTTGCTTCTAGTCATTTTTTTTACCA
GTTTTTCAAGCTCTATTTTATGGTAAAAAGGTGTCCTGGTAAAAATGGATGAA
TGGGTCTCATTCTCAGCAGACAATGTTTGAATGAGAAAGAAATAATTTTAAAC
TTTTTATACACTTTGCTTCTAGATTGATTGGGACTAGTCGAATAAAATCTTAG
TAGAGGTCTAAGGAAACATGATACACATCTTGTTTGGTTGAAATCTTACCATT
GTTTTTGGTTTCAGTTATTGATCTGGTTTTTGGACTACTTTTTCTGCAACTAT
TTGAGAATGAGAAATTACTTACCAAAAAAAGAAAGTCTTCATCTACGCCAAG
GATTTAGAATATTCGTACATGAATTTTGATTTCCAGTACATTGCGTCATGAAC
TATATAGTCTACTTGTTTTTTTTGTATCTATTTGACATGCAGCAAAGCCAGC
AACACATCTTTTATTGAGTCTGATGATATTTGTGAACTAATTCGAAAATATTT
AAAAGATTCGAGTGTATGAAGGTTTAACTATTATCAAAATCTCTAGATATTT
CAACTGATGGCAACACTCAACAATCTCACAATCACGACATAAAAATCCAATAAC
ACTTGAAACCAAAAGAGGGTTCAAATTAGGGTTTCTTGTTAAATCGAAATTGG
ACTTTTATTTATTTATTAACATCTGACTTTTGAGTTTTGACCAAAAAAAAAGA
TGGAAAATATCGCTTTGAAATTGAGGACCCAAAGGAAACGTAAATATGCCGAC
CAATCAACCATATACCAAAAATTGATATGTGGCTATGTCCCCACCACCACCACC
TATCATATCACAAGTTCTCTCTACTTTTCTCCGAATTTTACCACCCAATCAAAA
CGCTTCTCTCTTCTTCTACTTCTTCACTTCTCTCTCCTTCAACAAAATTTTCTA
ccctttgtttcttctctcagatttcataaagaaaagatttaatctttcattggaatctgtgagtaacagaggataagcgaat
```

FIG.3

PLANT SENESCENCE-SPECIFIC GENE AND ITS PROMOTER

This application claims priority from Korean Patent Application No. 2004-0069765 filed on Sep. 2, 2004.

FIELD OF THE INVENTION

The present invention relates to a novel senescence-specific gene derived from *Arabidopsis thaliana* and a promoter thereof. More particularly, the present invention relates to a plant senescence-specific gene available for controlling plant aging in an environment-friendly manner and a promoter for regulating the expression of the plant senescence-specific gene.

DESCRIPTION OF THE PRIOR ART

The life of creatures, e.g., birth, senescence, disease, and death, is the most interesting and important subject of life sciences. Of the life processes, senescence is a natural part of the development and eventual death of creatures. Thus, with the eventual aim of the retardation of senescence in living organisms, active and extensive research has been and is being conducted on causes and control mechanisms of senescence all over the world. However, no great account has been taken of the results obtained thus far.

Studies on the control mechanisms of senescence-related genes in plants as well as animals are underway. The senescence of higher plants, which is a part of the programmed cell death process (PCD), is observed in all plant tissues including leaves and flowers as a last stage of development, and occurs locally to defend against external attacks. It has been reported that plant senescence is under the control of hormones, such as ethylene, abscisic acid and cytokinins, and is also regulated by sugar metabolism.

Genes involved in the induction or retardation of plant senescence, when its molecular mechanisms are revealed, may be of great interest to the botanical industry. For example, when plant senescence-related genes are introduced, flowering plants such as roses, carnation, etc. or food plants such as rice, wheat, barley, etc. could have prolonged life spans. That is, plant senescence can be retarded in an environment-friendly manner. With these purposes, active research on plant senescence-related genes and promoters for regulating the expression of the genes is being conducted using *Arabidopsis thaliana*.

Korean Pat. Laid-Open Publication No. 10-2004-0023252 relates to an SOR9 gene isolated from a mutant that was found to show higher accelerated leaf senescence than the ore9-1 mutant, delaying the onset of hormone-induced leaf senescence, as revealed by activation tagging.

A lot of difficulty is encountered in studying senescence-related genes because they are highly involved in plant development and growth. Hence, CaMV (Cauliflower mosaic virus) 35S promoter, which is most frequently used in plant transformation, is not suitable for the study of plant senescence.

Until recently, the promoters of the genes which are known to be temporarily expressed upon artificial treatment with chemicals or hormones have been utilized in transformation studies with senescence-related genes. However, in addition to having a bad influence on plants themselves, chemical treatment can make only a guess to the functions of senescence-related genes. Furthermore, the inability of chemicals to be permanently anchored in plants is a critical weakness limiting their practical use.

Such limitations give a request for a gene promoter that is specific for plant senescence. In 1995, a promoter was reported to regulates SAG12 (senescence-associated gene 12), which is responsible for senescence in *Arabidopsis thaliana*. Additionally, only a few genes, including SEN4, have been found to be under the control of such promoters that are responsible for senescence-specific regulation hitherto [Gan S and Amasino R M, 1995, Inhibition of leaf senescence by auto-regulated production of cytokinin. Science 270: 1986–1988, Noh Y S and Amasino R M, 1999, Identification of a promoter region responsible for the senescence-specific expression of SAG12. Plant Mol Biol 41: 181–194].

Therefore, there is an increasing need for a promoter that exhibits an auto-regulated reaction in response to senescence without external aid, with which not only can senescence-related genes be effectively analyzed for functionality in a short time without influencing the development and growth of plants, but also plants can be permanently transformed in an environmentally friendly manner.

SUMMARY OF THE INVENTION

Leading to the present invention, intensive and thorough research on the control mechanisms of plant senescence-related genes, conducted by the present inventors, resulted in the finding that a novel gene is strongly expressed in the presence of salicylic acid under the control of a novel promoter and thus that the novel gene in combination with the promoter can be used to control plant senescence in an environmentally friendly manner.

Therefore, it is an object of the present invention to provide a novel gene that shows plant senescence-specific expression and a promoter that can induce the expression of the gene.

It is another object of the present invention to provide a novel recombinant vector comprising the plant senescence-specific gene along with the promoter, and a transgenic plant species transformed with the recombinant vector.

In accordance with an aspect of the present invention, the above objects could be accomplished by a provision of a plant senescence-specific gene, comprising a nucleotide sequence of SEQ ID NO: 1 or a nucleotide sequence substantially homologous to SEQ ID NO: 1.

In accordance with another aspect of the present invention, the above objects could be accomplished by a provision of a promoter, capable of inducing senescence-specific expression in plants, comprising a nucleotide sequence of SEQ ID NO: 2 or a nucleotide sequence substantially homologous to SEQ ID NO: 2.

In accordance with a further aspect of the present invention, the above objects could be accomplished by a provision of a recombinant vector comprising the promoter nucleotide sequence.

In accordance with still a further aspect of the present invention, the above objects could be accomplished by a provision of a microorganism transformed with the recombinant vector.

In accordance with yet another aspect of the present invention, the above objects could be accomplished by a provision of a transgenic plant transformed with the microorganism.

BRIEF DESCRIPTION OF DRAWINGS

FIG. 2 is the entire nucleotide sequence (SEQ ID NO: 1) of a gene which is expressed specifically in senescent plant tissues.

FIG. 3 is the entire nucleotide sequence (SEQ ID NO: 2) of a promoter which is a promoter functioning to include the expression of the plant senescence-specific gene.

DETAILED DESCRIPTION OF PREFERRED EMBODIMENTS

The genomic DNA of *Arabidopsis thaliana* has been completely sequenced. On the basis of the DNA sequence revealed, information about the positions of genes, and important domains, exons and introns has been inferred and is freely available. However, the genes of *Arabidopsis thaliana*, for the most part, remain unrevealed with regard to function and particular domains.

In the research conducted by the present inventors, *Arabidopsis thaliana* was treated with salicylic acid, a plant hormone which plays an important role in stress-related response, to seek for senescence-related genes. As a result, an unknown gene which has its expression increased with salicylic acid treatment was found and named AtCDCP1.

TAIR (The *Arabidopsis* Information Resource) BLAST search resulted in the detection of the gene (TAIR No. at4g34120), which shares almost complete homology with AtCDCP1 (see FIG. 2).

Inferred to be responsible for the regulation of senescence-specific expression, a putative promoter of this gene was isolated and base-sequenced (see FIG. 3).

To determine whether this putative promoter is able to induce senescence-specific expression, GUS was linked to the promoter, followed by the expression of the recombinant gene. In result, GUS was observed only in senescent leaves (see FIG. 5).

Hence, the novel promoter of the present invention, isolated from *Arabidopsis thaliana*, was identified to be almost latent in normal tissues but induce senescence-specific expression, so that it can be usefully utilized in controlling senescence in an environment-friendly manner.

In the present invention, nucleotide sequences substantially homologous to SEQ ID NO: 1 or SEQ ID NO: 2 refer to those that have any substitution of, variation of, modification of, replacement of, deletion of or addition of one or more nucleotides, but retain same activities relating to senescence-specific expression.

Figure 4:
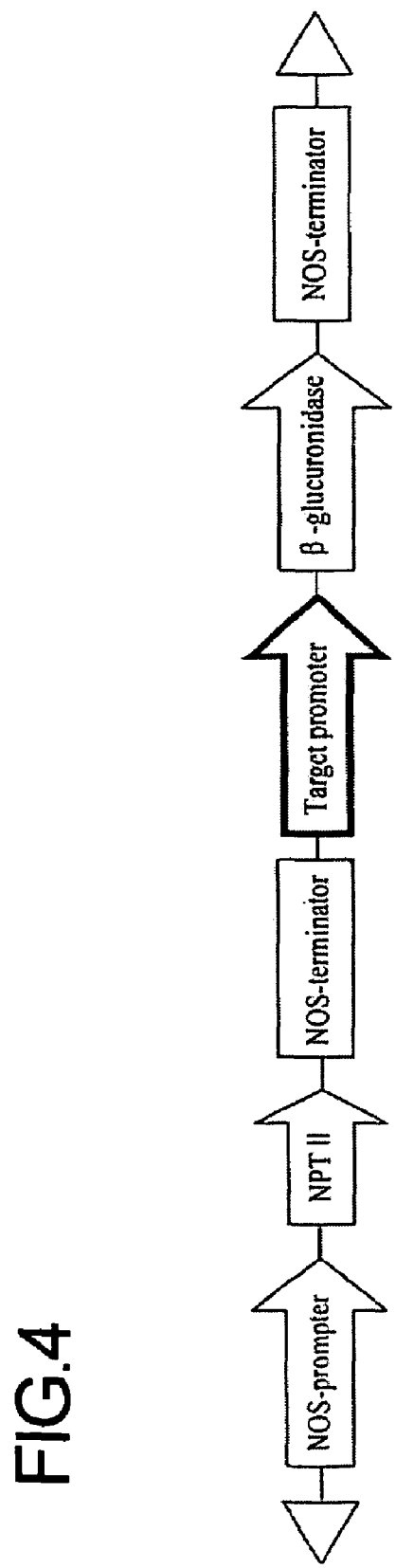
FIG. 4 is a schematic diagram showing a pBI101 vector consisting of a left boarder and a right boarder, useful in cloning the promoter inducing the expression of the plant senescence-specific gene.
Figure 5:
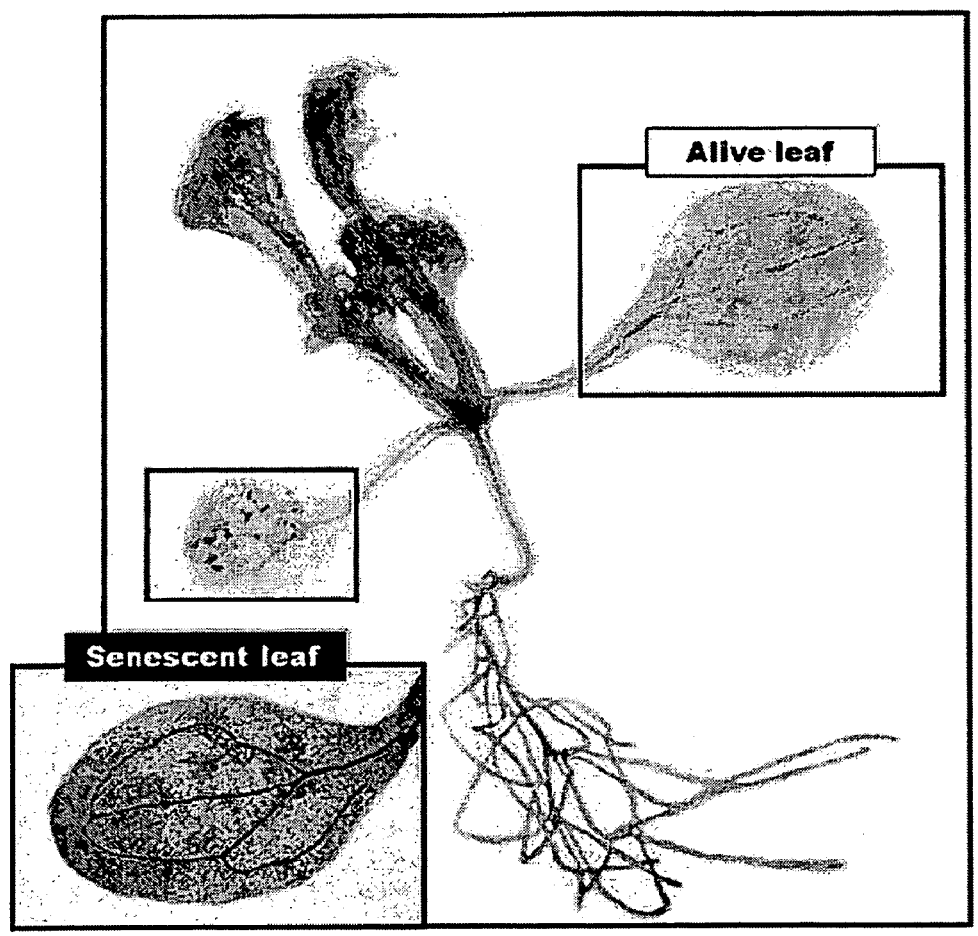
FIG. 5 is a microphotograph showing the expression of GUS fused to the promoter inducing the expression of the plant senescence-specific gene, according to leaf senescence.

Additionally, the present invention pertains to a recombinant vector containing the nucleotide sequence of the promoter (see FIG. 4) and a plant transformed with the recombinant vector (see FIG. 5).

Various techniques known to those skilled in the art are available for the production of a recombinant vector containing the promoter of the present invention and the introduction into plants thereof. For example, a technique for Agrobacterium-mediated transformation may be utilized (reference: Clough S J and Bent A F, 1998, Floral dip: a simplified method for Agrobacterium-mediated transformation of *Arabidopsis thaliana*. Plant J 16:735–43).

Furthermore, the present invention is concerned with a set of PCR primers, represented by SEQ ID NOS: 5 and 6, for a DNA fragment containing the nucleotide sequence of SEQ ID NO: 2.

A better understanding of the present invention may be obtained in light of the following examples which are set forth to illustrate, but are not to be construed to limit the present invention.

EXAMPLE 1

Discovery of Novel Gene AtCDCP1

When *Arabidopsis thaliana* was treated with the stress-related plant hormone salicylic acid, over-expression was induced in a gene, which had not been previously known, and this unknown gene was called AtCDCP1.

A Blast search on TAIR (The *Arabidopsis* Information Resource) site found that the gene TAIR No. at4g34120 is in 100% homology with AtCDCP1.

EXAMPLE 2

RT-PCR of Target Gene (TAIR No. at4g34120)

To examine whether the open reading frame (ORF) of the AtCDCP1 gene identified on TAIR site is transcribed in practice in *Arabidopsis thaliana*, RT-PCR was performed.

For RT-PCR, cDNA was synthesized from the total RNA which was extracted from each tissue of *Arabidopsis thalina* (ecotype Columbia), e.g., flower, cauline leaves, rosette leaves, stem, and root, with the aid of the Nucleospin RNA plant kit (Macherey-Nagel).

A mixture of 4 µg of the total RNA, 10 mM each of dNTPs, 100 M random decamer, and nuclease-free water was incubated at 65° C. for 5 min, and then placed on ice. After the addition of an RT-PCR buffer, an RNase inhibitor and 0.1 M DTT, the mixture was further incubated at 42° C. for 2 min.

Then, the mixture was placed back on ice, followed by incubation with 200 units of a reverse transcriptase at 42° C. for 1 hr. Following inactivation at 70° C. for 15 min, the reverse transcription product was used as a cDNA pool. In the same manner, cDNA pools were made according to tissues. They were used as templates for RT-PCR.

RT-PCR primers were synthesized from the exon regions of the target gene on the basis of the nucleotide sequence identified on the TAIR site. RT-PCR Primers specific for the target gene are given in Table 1, below. The PCR amplification was performed using Gene Amp® PCR System 2700 (Perkin Elmer, USA) in a touchdown PCR manner in which thermal cycling conditions were as follows: 95° C., 2 min, followed by 5 cycles of 95° C., 40 sec; annealing temperature stepdowns every cycle of 1° C. from 62° C. to 57° C., 15 sec; 72° C., 1 min and then in a standard PCR manner in which thermal cycling conditions were as follows: 20 cycles of 95° C., 40 sec; 57° C., 15 sec; 72° C., 1 min, followed by 72° C., 5 min.

TABLE 1

RT-PCR Primers Specific for Target Gene

| | | |
|---|---|---|
| 5'CCT-CTA-CGT-CGG-TCG-ATG-ATG-CG | (SEQ ID NO:3) | 23-mer |
| 5'CCA-TAT-GTC-TTA-CTG-ATC-AGT-TTC-TGT-AGT-TCG | (SEQ ID NO:4) | 33-mer |

Figure 1:
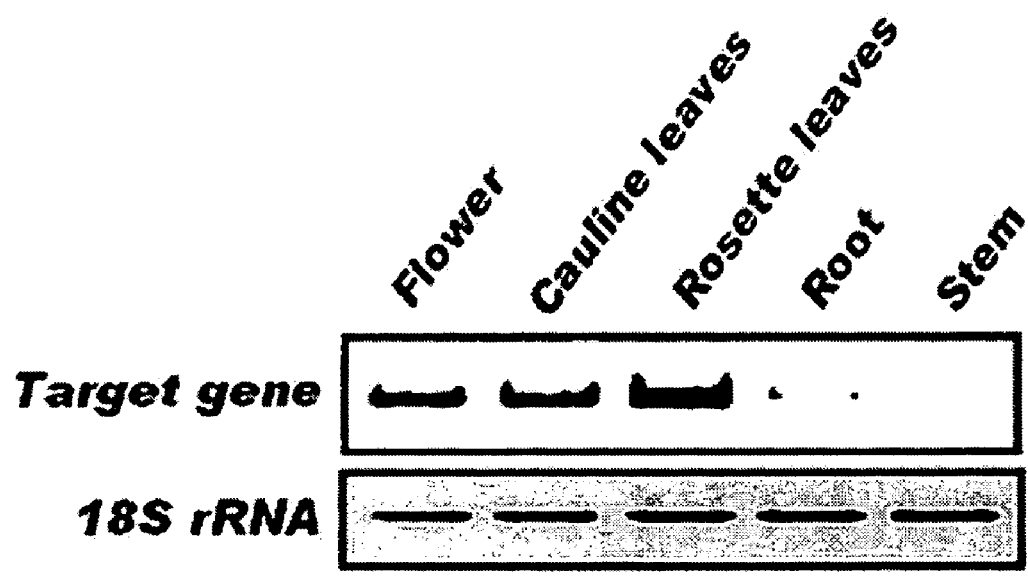
FIG. 1 is a photograph of an RT-PCR result showing the transcription of the plant senescence-specific gene in various plant tissues.

As an internal control, 18s rRNA (Ambion) was observed to be expressed in the same quantity in the cDNA pools according to tissue. Results of the RT-PCR with the target gene-specific primers are shown in FIG. 1. As seen in FIG. 1, strong expression of the target gene was observed in flower, cauline leaves and rosette leaves.

EXAMPLE 3

Identification of the Promoter for Senescence-Specific Gene (TAIR No. at4g34120)

The promoter of the target gene (at4g34120) was assumed to correspond to the 1,094 base pairs which span from the 3'UTR (untranslated region) of the gene at4g34110, just upstream of the AtCDCP1 gene (at4g34120), to the start codon (ATG) of the target gene (at4g34120).

First, genomic DNA (gDNA) was extracted from *Arabidopsis thaliana*. A couple of primers, represented by SEQ ID NOS: 5 and 6, were designed to each have HindIII at the 5' terminus and BamHI at the 3' terminus (see Table 2). Using a DNA polymerase (pyrobest, TAKARA) having proofreading activity, the putative promoter region was amplified in cooperation with the primers, with the gDNA serving as a template. PCR amplification was performed using Gene Amp® PCR System 2700 (Perkin Elmer, USA) in a touchdown PCR manner in which thermal cycling conditions were as follows: 95° C., 2 min, followed by 5 cycles of 95° C., 40 sec; annealing temperature stepdowns every cycle of 1° C. from 60° C. to 55° C., 15 sec each temperature; 72° C., 1.5 min and then in a standard PCR manner in which thermal cycling conditions were as follows: 30 cycles of 95° C., 40 sec; 55° C., 15 sec; 72° C., 1.5 min, followed by 72° C., 30 sec.

TABLE 2

Primers for Cloning the Promoter

| | | |
|---|---|---|
| 5'-CTA-AAG-CTT-GTG-TTC-ACG-GAA-GAT-GAA-TTT-GAT-T | (SEQ ID NO:5) | 34-mer |
| 5'-CAT-GGA-TCC-ATT-CGC-TTA-TCC-TCT-GTT-ACT-CAC-AGA | (SEQ ID NO:6) | 36-mer |

After its termini were cut with proper restriction enzymes, the PCR product was cloned into a pBl101 vector. Base sequencing revealed that the target promoter was isolated accurately (see FIG. 3).

EXAMPLE 4

Cloning and Senescence-Specific Expression of the Target Promoter

For cloning of target promoter, the pBl101 vector is a binary vector that is capable of plant transformation and has a GUS(β-glucuronidase) reporter gene between a left boarder and a right boarder (see FIG. 4). First, this binary vector containing the target promoter was introduced into Agrobacterium (GV3101). *Arabidopsis thaliana* was transformed with this Agrobacterium by a flower dipping method (Clough et al., Plant J., 16(6): 735–743, 1998).

By screening the *Arabidopsis thaliana* transformants three times, a transgenic $T_3$ line was obtained. Having the activity of hydrolyzing a specific substrate (X-GlcA) into a blue water-insoluble precipitate, GUS(β-glucuronidase) is utilized as a reporter for determining whether the GUS gene is introduced into a plant tissue of interest because when the GUS gene is expressed, a plant tissue harboring the GUS gene turns blue in an X-GlcA buffer.

No normal living leaves appeared blue, but only senescent (chlorophyll-absent) leaves were observed to strongly express the GUS gene (see FIG. 5). Observation through a microscope with high magnification power revealed that the target promoter is specific for senescence.

As described hereinbefore, the present invention provides the novel gene AtCDCP1, which shows senescence-specific expression, and a novel promoter which regulates the senescence-specific expression. Using the expression of the novel gene under the control of the promoter, plants can be effectively analyzed for functions of senescence-related genes in a short time without influence thereon in addition to being permanently transformed into new species in an environmentally friendly manner.

What is claimed is:

1. An isolated promoter, which induces senescence-specific expression in plants, comprising the nucleotide sequence of SEQ ID NO: 2.

2. A recombinant vector, comprising the promoter of claim 1.

3. A transgenic plant, transformed with the vector of claim 2.

4. The isolated promoter of claim 1, wherein the promoter is amplified by a primer pair consisting of SEQ ID NOS: 5 and 6.

* * * * *

SEQUENCE LISTING

```
<160> NUMBER OF SEQ ID NOS: 6

<210> SEQ ID NO 1
<211> LENGTH: 1175
<212> TYPE: DNA
<213> ORGANISM: Arabidopsis thaliana

<400> SEQUENCE: 1
ctacctttgt ttcttctctc agatttcata aagaaaagat ttaatctttc attggaatct      60
gtgagtaaca gaggataagc gaatatgggt tcaatctctt tatccaattc tatgcccata     120
```

-continued

| | |
|---|---|
| actcgacttc cactacttac atcactctat catcaaagct tccttccgat ttcttcttca | 180 |
| tctttctctc ttcttcctct ctctaatcgt cgtcgctcct ccacttttc accgtcaatc | 240 |
| accgtctctg ccttcttcgc tgctcctgcc agcgttaata ataataactc tgttccggca | 300 |
| aaaaatggag gttacacagt tggggatttc atgactccga gacagaattt gcacgttgtt | 360 |
| aagccctcta cgtcggtcga tgatgcgttg gaacttctgg ttgagaagaa agtcacggga | 420 |
| ttgcctgtaa ttgacgataa ttggacactg gttggtgttg tttctgatta cgatttgctt | 480 |
| gcattggact ccatctctgg tcgcagtcaa aatgatacaa acttgttccc tgatgtcgac | 540 |
| agtacctgga aaacgtttaa cgaactacag aaactgatca gtaagacata tggaaaagtt | 600 |
| gttggagact tgatgacacc gtctcctctc gttgtccgtg attctaccaa tttagaagat | 660 |
| gcagccaggt tgcttctgga aacaaagttc gaagattac ccgttgttga tgctgatgga | 720 |
| aaactgattg ggatccttac aaggggaaac gttgtaaggg ctgcgctgca gatcaaacgg | 780 |
| gaaaccgaga actctacata gctaggaagc agcagtgatg gagcagatct gaatctgcca | 840 |
| tagttaatag cgaaatctat ttattccatt gatataagta tatatgtaac cattctctgt | 900 |
| caattttcgg ttttcagaag caattttttgt tactttagga gtaacatttc tcagactcgg | 960 |
| aactgaagac aaatggtata tttgatacat atatgtttat tgtagcacag gtctactctt | 1020 |
| atcaccaaga caaagactaa gcagaatcga actaattttc aatttcttac tgaggtctttt | 1080 |
| tcaatgaagc tattcaaatc gagaaacgaa gacccttttt tctccaccgc cggctttggc | 1140 |
| catcacagcc tcttctctgc catattctct gctta | 1175 |

<210> SEQ ID NO 2
<211> LENGTH: 1094
<212> TYPE: DNA
<213> ORGANISM: Arabidopsis thaliana

<400> SEQUENCE: 2

| | |
|---|---|
| gtgttcacgg aagatgaatt tgattaccaa taaggccaat gctggtgatc ccctctttg | 60 |
| gccttttgac tgttggtggt tgttgcttct agtcattttt tttaccagtt tttcaagctc | 120 |
| tattttatgg taaaaaggtg tcctggtaaa aatggatgaa tgggtctcat tctcagcaga | 180 |
| caatgtttga atgagaaaga aataatttta aacttttat acactttgct tctagattga | 240 |
| ttgggactag tcgaataaaa tcttagtaga ggtctaagga aacatgatac acatcttgtt | 300 |
| tggttgaaat cttaccattg ttttttggttt cagttattga tctggttttt ggactacttt | 360 |
| ttctgcaact atttgagaat gagaaattac ttaccaaaaa aaagaaagtc ttcatctacg | 420 |
| ccaaggattt agaatattcg tacatgaatt tgatttcca gtacattgcg tcatgaacta | 480 |
| tatagtctac ttgttttttt ttgtatctat ttgacatgca gcaaagccag caacacatct | 540 |
| tttattgagt ctgatgatat ttgtgaacta attcgaaaat atttaaaaga ttcgagtgta | 600 |
| tgaaaggttt aactattatc aaaatctcta gatatttcaa ctgatggcaa cactcaacaa | 660 |
| tctcacaatc acgacataaa aatccaataa cacttgaaac caaagagggg ttcaaattag | 720 |
| ggtttccttgt taaatcgaaa ttggactttt atttatttat taacatctga cttttgagtt | 780 |
| ttgaccaaaa aaaagatgg aaaatatcgc tttgaaattg aggacccaaa ggaaacgtaa | 840 |
| atatgccgac caatcaacca tataccaaaa attgatatgt ggctatgtcc ccaccaccac | 900 |
| cacctatcat atcacaagtt ctctctactt ttctccgaat tttaccaccc aatcaaaacg | 960 |
| cttctctctt cttctacttc ttcacttctc tctccttcaa caaaattttc tacccttttgt | 1020 |
| ttcttctctc agatttcata aagaaaagat ttaatctttc attggaatct gtgagtaaca | 1080 |

-continued

```
gaggataagc gaat                                              1094

<210> SEQ ID NO 3
<211> LENGTH: 23
<212> TYPE: DNA
<213> ORGANISM: Artificial Sequence
<220> FEATURE:
<223> OTHER INFORMATION: Primer for PCR

<400> SEQUENCE: 3
cctctacgtc ggtcgatgat gcg                                      23

<210> SEQ ID NO 4
<211> LENGTH: 33
<212> TYPE: DNA
<213> ORGANISM: Artificial Sequence
<220> FEATURE:
<223> OTHER INFORMATION: Primer for PCR

<400> SEQUENCE: 4
ccatatgtct tactgatcag tttctgtagt tcg                           33

<210> SEQ ID NO 5
<211> LENGTH: 34
<212> TYPE: DNA
<213> ORGANISM: Artificial Sequence
<220> FEATURE:
<223> OTHER INFORMATION: Primer for PCR

<400> SEQUENCE: 5
ctaaagcttg tgttcacgga agatgaattt gatt                          34

<210> SEQ ID NO 6
<211> LENGTH: 36
<212> TYPE: DNA
<213> ORGANISM: Artificial Sequence
<220> FEATURE:
<223> OTHER INFORMATION: Primer for PCR

<400> SEQUENCE: 6
catggatcca ttcgcttatc ctctgttact cacaga                        36
```